(12) United States Patent
Alford

(10) Patent No.: US 8,800,898 B2
(45) Date of Patent: Aug. 12, 2014

(54) METHOD AND APPARATUS FOR PROCESSING OF MATERIALS

(75) Inventor: Paul Alford, Hammond, LA (US)

(73) Assignee: Tempico Manufacturing, Inc., Hammond, LA (US)

(*) Notice: Subject to any disclaimer, the term of this patent is extended or adjusted under 35 U.S.C. 154(b) by 648 days.

(21) Appl. No.: 12/950,656

(22) Filed: Nov. 19, 2010

(65) Prior Publication Data

US 2011/0121112 A1    May 26, 2011

Related U.S. Application Data

(60) Provisional application No. 61/262,715, filed on Nov. 19, 2009.

(51) Int. Cl.
*B02C 23/24* (2006.01)
*B03B 9/06* (2006.01)
*A61L 11/00* (2006.01)
*B09B 3/00* (2006.01)

(52) U.S. Cl.
CPC . *B03B 9/06* (2013.01); *A61L 11/00* (2013.01); *B09B 3/00* (2013.01); *B09B 3/0083* (2013.01)
USPC .............................. 241/18; 241/23

(58) Field of Classification Search
USPC ................. 241/23, 284, 299, DIG. 38, 65, 18
See application file for complete search history.

(56) References Cited

U.S. PATENT DOCUMENTS

| | | |
|---|---|---|
| 4,974,781 A | 12/1990 | Placzek |
| 5,009,370 A | 4/1991 | Mackenzie |
| 5,119,994 A | 6/1992 | Placzek |
| 5,190,226 A | 3/1993 | Holloway |
| 5,556,445 A * | 9/1996 | Quinn et al. ...................... 71/11 |
| 5,779,164 A | 7/1998 | Chieffalo et al. |
| 6,306,248 B1 | 10/2001 | Eley |
| 6,379,527 B1 | 4/2002 | Vogt et al. |
| 6,588,690 B1 | 7/2003 | Koenig |
| 6,752,337 B2 | 6/2004 | Koenig |
| 7,040,557 B2 | 5/2006 | Graham et al. |
| 7,226,006 B2 | 6/2007 | Porter et al. |
| 2008/0202993 A1 | 8/2008 | Eley et al. |

* cited by examiner

*Primary Examiner* — Mark Rosenbaum
(74) *Attorney, Agent, or Firm* — Brett A. North; Garvey, Smith, Nehrbass & North, L.L.C

(57) ABSTRACT

A method and apparatus processing materials including municipal waste at ambient pressure and low temperatures, and processing materials; the apparatus comprising an elongated rotating cylindrical configuration.

20 Claims, 7 Drawing Sheets

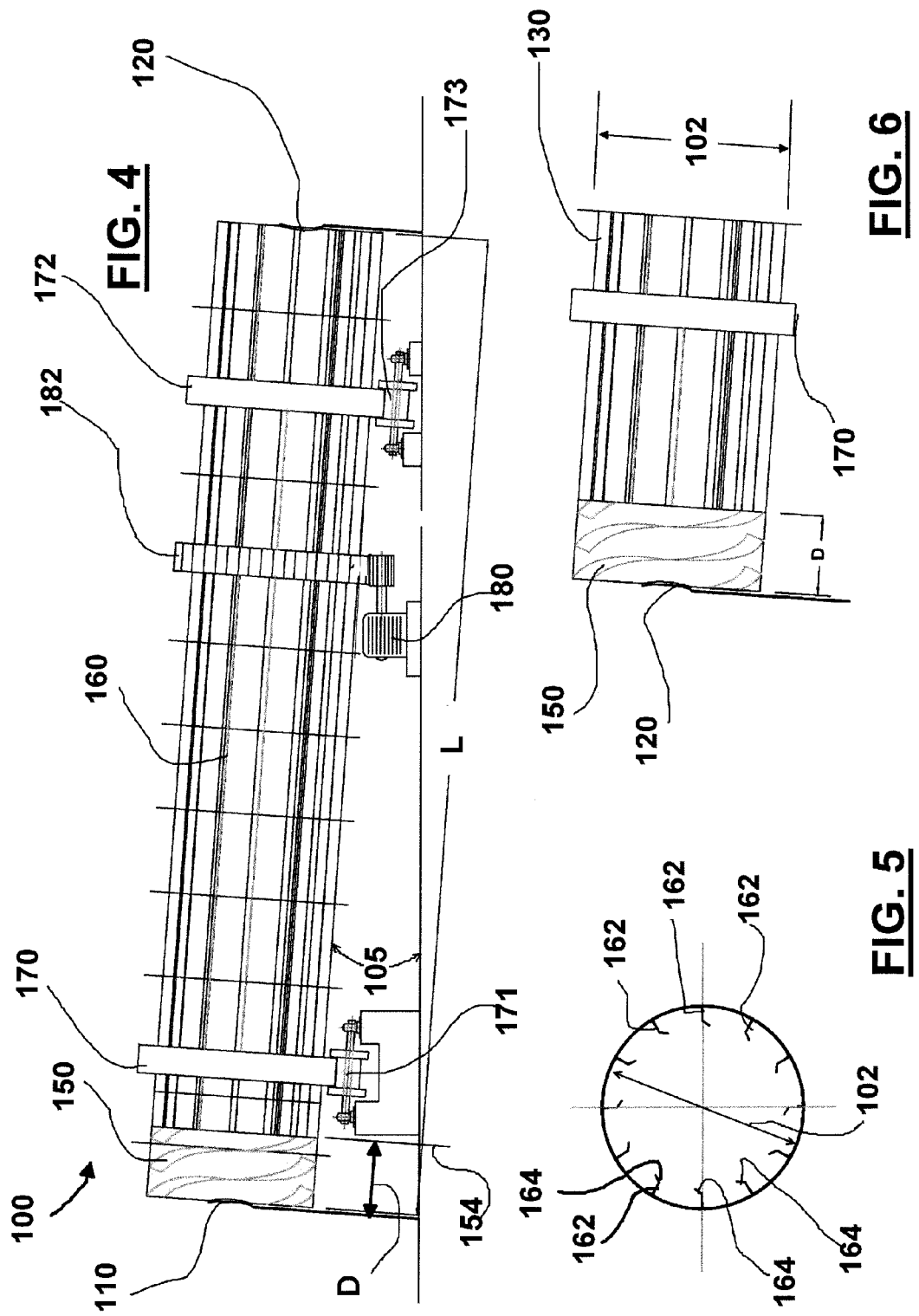

METHOD AND APPARATUS FOR PROCESSING OF MATERIALS

CROSS-REFERENCE TO RELATED APPLICATIONS

This is a non-provisional of U.S. Provisional Patent Application Ser. No. 61/262,715, filed Nov. 19, 2009, which application is incorporated herein by reference, and priority of which is hereby claimed.

Priority of U.S. Provisional Patent Application Ser. No. 61/262,715, filed Nov. 19, 2009, which application is incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND

U.S. Pat. Nos. 5,119,994 and 4,974,781 are incorporated herein by reference.

Rising concerns regarding proper handling and disposal of waste materials continues to occur.

Waste paper has been recycled and used as a source of feedstock for the manufacture of paper products. The availability of recycled paper, however, is subject to the economics of the recovery, sorting, and cleaning of the waste paper from the waste paper containing materials requiring sorting of the paper at the source of generation and special handling by the generator; dedicated pickup of specially segregated materials by a recycler; and component separation by the recycler after collection.

Waste plastics have become increasingly important because of their very long term resistance to degradation and decomposition in the environment and because of the hazardous nature of the gaseous compounds that are produced when plastics are produced or later incinerated. The recovery, sorting, and cleaning of waste plastics for recycling, as with waste paper, typically also requires sorting of the plastic at the source of generation and dedicated pickup of specific plastics by a recycler to be viable as a source of plastic to be utilized by the plastics industry.

It has long been recognized that the achieving of a method of separating waste paper and plastics as well as recyclable metals from the extraneous contaminating components that typically accompany a paper containing waste material would be highly desirable. This is particularly true if the paper and plastic containing waste material is municipal solid waste. Municipal solid waste typically contains 25-60% paper materials along with a varying assortment of glass, metals, rags, food wastes, plastics, etc. It is believed that typical component compositions for municipal solid wastes are as follows:

TABLE 1

| Paper | 35% |
|---|---|
| Metals | 8.0% |
| Plastic | 11.3% |
| Glass | 5.3% |
| Food Waste | 11.7% |
| Grass Clippings | 12.1% |
| Wood | 5.8% |
| Leather, Textiles, and Rubber | 7.4% |
| Other | 3.4% |
| TOTAL | 100.0% |

It is believed that much of metals, paper and plastic containing waste materials are being landfilled, resulting in the loss of paper and recyclable materials and the using up of valuable land space. Landfills also threaten the environment with contamination of surface and groundwater, and present health hazards and public nuisances by increasing numbers of disease-carrying birds, rodents and insects. Once in landfills, the organic fraction of municipal solid waste degrades to form methane, a particularly hazardous source of fugitive emissions from landfills, which is a major contributor to global warming. The problem is an ever-increasing one. By their existence, municipalities and industries generate paper-containing and plastic-containing wastes continually and these wastes must be properly disposed of. Various approaches such as incineration, composting, and producing refuse-derived fuel have been considered as alternative solutions to landfills.

Incineration, although it can reduce the amount of landfilling required, produces undesirable and hazardous pollutants released in the air, primarily by the combustion of plastics contained in the waste materials and the volatilizing of metals such as aluminum contained therein. Incineration also produces relatively few products generating revenue except for energy sales of steam and electricity, which are dependent on adjacent customers and subject to rates set by local public utilities, causing most of the costs related to incineration facilities to fall on the public attempting to deal with the waste streams.

Composting, which is the process of subjecting waste materials to microbial action to produce a soil-like material is believed to have potential only as a soil conditioner. Because it contains relatively little nutrient value, compost cannot compete as a fertilizer. Additionally, the potential concentration of heavy metals in compost may be unacceptable considering that these may be absorbed into plants, and up the food chain.

Producing refuse-derived fuel from waste materials requires that a series of steps be taken to separate combustible materials from non-combustible materials. Separation results in several classification processes, producing a number of low quality products of limited value. The refuse-derived fuel produced contains plastics and potentially high levels of inorganic contamination which produce undesirable and hazardous pollutants released to the atmosphere when combusted.

Because of problems inherent in present methods of waste disposal, the continuing need to dispose of waste materials, and the need to recover valuable products currently being lost, there is a need to provide improved methods of separation and recovery of component fractions from waste paper and plastic containing materials.

Prior art MSW recycling systems re-pulp paper and paperboard fractions of MSW in pressurized and/or high temperature environments increasing utility costs and raising capital investment amounts. Prior art systems MSW treatment temperatures exceed 220 degrees Fahrenheit using pressurized steam or other hot gases, along with the addition of water, to facilitate the re-pulping the paper and paperboard contained in MSW for later screen separation. In these prior art systems, after the entire mixed MSW stream is size reduced (or pulped), organic materials are then screen separated from inorganic recyclables such as ferrous metals, aluminum and glass, and plastics. Prior art batch based autoclaves and other high temperature constant flow processing systems typically operate under relatively low to moderate pressure (substantially above atmospheric to 100 pound per square inch gauge) and moderate temperatures (between 220 & 400 degrees Fahrenheit). These high temperatures and pressures increase the cost of the prior art systems.

Currently, in many countries (including the US) there are no regulatory requirements for pressure treatment or high temperature sterilization of mixed household garbage (MSW). Accordingly, there is a need for a low pressure and low temperature MSW treatment system in order that MSW sorting and recycling is commercially viable in low tipping fee regions of the United States as well as globally in economically challenged countries.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the invention is critical or essential unless it is expressly stated as being "critical" or "essential."

SUMMARY

"Pulpable materials" mean those materials that when subjected to heat, moisture or agitation or any combination of those reduces to a pulpy mass.

"Municipal Solid Waste or MSW" means household and light commercial garbage not to include construction or demolition debris, large yard waste (stumps, tree trunks or large limbs), electronic recyclables, household hazardous waste (or other industrial or commercial hazardous waste) or white goods (sofas, refrigerators, washers or other large appliances).

"Recycled Paper" means all of those materials that consist of the product of cellulosic fibers that have been reduced to pulp and reconstructed into containers, wrappers, or materials to write on.

"Plastic" means organic, synthetic or processed materials including resins, foams, films, sheets and alloys (composites) that are molded, cast, extruded, drawn or laminated into objects or films.

A condition known to those skilled in the art as "segregation" occurs in a rotating cylinder or drum processing non-homogeneous and variable sized materials. "Segregation" is the phenomenon in which a rotating cylinder or drum causes materials of different size and density to separate and stratify according to size and density, with the smallest, most dense particles migrating to the bottom of the mass of materials and the largest and lowest density particles rising to the top of the mass of materials in the rotating cylinder or drum, with layers of intermediate sized and dense particles being sandwiched between them. The result of "segregation" is that the particles in the middle of the mass of materials can be insulated from the reactive environment of the rotating cylinder or drum, and not adequately treated.

One embodiment includes the introduction of waste material into a processor, equipped with a rotatable cylinder or drum. The interior of the rotating cylinder can be equipped with a series of upsets, lift plates or buckets causing a high degree of agitation of the materials to be processed when the rotating cylinder is rotated. The waste introduced into the processor in its undisturbed bags can be agitated by rotating the interior rotating cylinder. The waste material can be treated with added moisture and/or heat while agitation of the waste materials continues.

In one embodiment, the rotating cylinder may be comprised of rolled metal.

In one embodiment, the rotating cylinder may be comprised of flat panels, with the number of panels determined by desired diameter of the vessel such as an eight foot diameter vessel constructed from flat panels may have an octagon configuration or eight equally sized panels and a twelve foot diameter vessel may have a decagon configuration with 10 equally sized panels. Larger diameters may have more flat panels used in fabrication. Such flat panel design for rotating cylinder should increase agitation and potentially lower vessel fabrication cost.

In one embodiment as the process continues, contacting of the materials with the added moisture in conjunction with agitation causes the moisture absorbable materials to break down into their repulped form causing a significant reduction of the overall volume of the waste materials.

In one embodiment adding moisture directly increases transfer of heat into the waste materials being processed, compared to a "dry treatment" state which can produce an insulating effect for at least pockets of the waste materials being treated.

One embodiment includes a generally cylindrical shell or drum mounted on bearings allowing rotation of the cylinder or drum around its horizontal axis. The upper end of the rotating cylinder can have an opening to receive materials to be processed. The rotating cylinder can be equipped with upsets, lift plates or buckets and helical flighting located on its interior, to facilitate agitation of material placed therein and to direct movement of the materials within the rotating cylinder.

One embodiment overcomes "segregation" and compaction through use of upsets, lift plates or buckets at various locations on the interior of the rotating cylinder. The lift plates and/or buckets can be attached to the interior perimeter to avoid appurtenances within the rotating cylinder restricting flow or entangling materials. The movement of materials within the rotating cylinder by the buckets can occur in concert with the rotation of the cylinder along with movement caused by the rotating cylinder's angle of incline or descent. Materials can be lifted by lift plates and/or each bucket in concert with the rotation of the cylinder and then discharged as cylinder rotation continues. Such a process tends to prevent segregation by causing thorough agitation of the materials being processed.

One embodiment provides a means for adding controlled amounts of moisture to the interior of the vessel during cylinder rotation, to enhance the penetration of heat into the moisture absorptive materials of the waste materials.

One embodiment provides several devices operatively connected to the rotating cylinder, such as water piping, and/or steam piping, and other instruments for monitoring the process.

In one embodiment the rotating cylinder can be inclined at a slight angle to the horizontal, with the potential use of a continuous helix to facilitate constant flow. In various embodiments the angle of inclination can be about 1, 2, 3, 4, 5, 6, 7, 8, 9, 10, 12, 14, 16, 18, and 20 degrees. In various embodiments the angle of inclination can be between any two of the above specified angles. In various embodiments the angle of inclination can be varied between any two of the above specified angles.

The upper end of the rotating cylinder can be an addition point for water, steam, and other materials which can be added. The amount of water to be added corresponds to the amount of material that is to be processed. The water will tend to be absorbed into the shredded or un-bagged MSW, in particular the water is absorbed into the paper and paperboard component of the waste and does not accumulate at the lower end of the rotating cylinder.

One embodiment provides independent heating of rotating cylinder by such means as being a double wall jacket with steam, hot oil, or some other heating medium. In one embodiment lift plates, buckets or upsets can cause an increased agitation of materials in the rotating cylinder. In one embodiment the buckets can be staggered from each other from section to section. This effective positioning of the buckets can also cause a more even loading of forces on the drive and support mechanisms of the rotating cylinder by virtue of the more even lifting of the materials by the buckets.

In one embodiment a method and an apparatus for the separation and the recovery of component fractions, especially pulped paper, paperboard, and other biogenic materials, plastics, metals and potentially textiles and glass from MSW. In one embodiment paper and plastic containing waste materials can be handled and introduced into the apparatus without prior size reduction, or separation and special handling of waste. In one embodiment it is necessary to remove from the waste stream, certain items such as wire, large textiles, large appliances, demolition rubble (commonly referred to as White Goods and Construction/Demolition Debris or C&D), etc.

In one embodiment paper-containing and plastic-containing waste material can be initially treated with moisture to achieve a minimum moisture content of 30% in the moisture absorptive materials by weight, with 65% to 80% moisture content of the moisture absorptive materials by weight being optimum. The moisture non-absorptive materials, such as metals, glass and plastics that may be present are ignored in the moisture addition calculations. The apparatus is then agitated by suitable means well known to those skilled in the art, in this case by rotation to accomplish agitation of the mixture to allow the moisture to have complete and intimate contact with the components in the waste material, thus to effect repulping of the paper and paperboard components. Heat may be applied to the mixture in the form of hot water that is added to achieve the desired moisture content, or by heat exchangers in the shell of the apparatus or installed inside the apparatus. Preferably, however, heat in the form of saturated steam is injected directly into the mixture within the rotating vessel. The addition of heat to a reaction, increases the rate of the reaction.

In one embodiment repulping can be accomplished in the presence of moisture, and agitation and the time of repulping is affected by the appropriate addition of heat. This results in a size reduction of the various and irregularly sized paper components in the mixture into a homogeneous pulp, and a corresponding increase in the bulk density of those pulped components that are able to be separated from the non-pulpable components in the mixture. Various components such as food wastes that are pulpable are partially hydrolyzed and pulped, and are incorporated into the pulped fluff of the paper components.

In one embodiment after repulping has been accomplished, the processed pulpable and non-pulpable components can be directed to classification equipment. Such classification equipment preferably includes trommels, magnetic separators, eddy current separators, flotation chambers, optical sorting systems and sorting tables effective to recover product streams. Additional methods of classification are known to those skilled in the art.

In one embodiment as the repulping is accomplished, the volume of materials is condensed to approximately one-third of the initial volume of the materials and as the repulping process is being conducted.

In one embodiment the apparatus is equipped with piping to facilitate the addition of moisture to the necessary concentration of the mixture of the materials, and the addition of heat to increase the rate of reaction.

In one embodiment is provided a method and apparatus for accepting substantially untreated paper-containing and plastic-containing waste material and, in a continuous unit operation, to accomplish repulping of the pulpable components in the waste material, thus to produce a homogeneous pulped product that screen separates readily from the non-pulpable components included in the waste material.

In one embodiment the method separates component fractions from paper-containing and plastic-containing waste materials. This embodiment can accepts materials of widely varying characteristics such as paper, plastics, glass, metal, food wastes and other materials to be inserted en masse into the rotating cylinder. Intimate contact of materials with moisture and heat can be accomplished, thus effecting repulping of paper and paperboard materials. The repulped materials, as a result of directional tumbling, are dispersed throughout the vessel. Because of the repulping of the pulpable materials, size reduction of randomly large and odd-shaped repulpable material is accomplished. By virtue of the size reduction of the large and odd-shaped pulpable materials, the non-pulpable components are freed of the larger particle shapes and surfaces that negatively affect screen separation. The pulping of the pulpable materials increases the bulk density of those materials, further enhancing their screen separation from the additional components. The recovered repulped product can be suitable for recycle fiber in the paper, paperboard or plastic building products industry; for combustion, gasification or pyrolysis as a high quality fuel, or for use as a feedstock for conversion into renewable liquid biofuels or specialty chemicals. The recovered non-pulpable materials such as plastics, glass, metals, aluminum and other materials can be suitable for recycling into their producer industries; as feedstock raw materials for additional manufacturing of products; or any or all of these materials can be disposed of in a sanitary landfill as is the commonly accepted practice.

In one embodiment is provided an ambient pressure, low temperature, constant flow MSW recycling system which is based around a rotating pulping unit and treatment equipment offering a more efficient and cost effective alternative to batch and/or higher temperature MSW processing and recycling systems.

In various embodiments the method and apparatus can perform adequate processing at significantly lower capital and operating costs than prior art MSW recycling systems, looking at steam, electricity, and water consumption and other associated operating costs. One reason for the significant reduction of capital and operating costs is operating at pressures which do not exceed ambient, which remove the need for and cost of a pressure vessel, while the method and apparatus can still fully pulp paper and paperboard component for easy screen separation and sanitizing the mixed MSW to a high degree by maintaining sufficient retention time within prescribed range of temperature.

In one embodiment is provided a method and apparatus which can process MSW for the separation of traditional recyclables such as ferrous metals, aluminum, textiles and plastics, while further processing the separated and recovered biomass component of the waste stream to specification, for use in multiple biomass conversion technology applications. In various embodiments particular applications for MSW treatment can include production of cellulosic ethanol, butanol, methanol, synthetic gasoline, synthetic diesel as well as other biofuels or specialty chemicals, steam and/or electricity via combustion, gasification or pyrolysis based systems.

In one embodiment is provided a method and apparatus that can saturate pre-shredded or unshredded, mixed MSW with hot water, and perform re-pulping of the paper and paperboard fractions in a rotating, constant flow vessel, at ambient pressure and in a low temperature heated mode of operation. In one embodiment heat to the rotating cylinder can be by steam. In one embodiment heat can be by saturated steam.

In one embodiment the method and apparatus can include a processing temperature being maintained between 160 degrees Fahrenheit to 210 degrees Fahrenheit at ambient pressure for a predefined retention time (e.g., minimum 30 minutes). In other embodiments the lower range of the processing temperature can be ambient temperature, or higher, about 120, 125, 130, 140, 145, 150, 155, and 160 degrees Fahrenheit. In the lowest temperature applications, the assumption is that recyclables would have already been recovered and that pulping is for the purpose of biomass preparation for downstream conversion to ethanol, butanol, methanol, synthetic gasoline or diesel, specialty chemicals or renewable electricity. In other embodiments the upper temperature can be about 180, 185, 190, 195, 200, 205, and 210 degrees Fahrenheit. In various embodiments the upper and lower temperatures of the range can be between any two of the above specified temperatures. The desired upper level of processing temperatures identified facilitates the achievement of a high level of sanitizing action, while performing the paper re-pulping process, and offering a much higher throughput and cost effectiveness compared to existing prior art high temperature constant flow or batch autoclave systems.

In various embodiments the retention time of the MSW after entering the rotating cylinder can be about 10, 15, 20, 25, 30, 35, 40, 45, 50, 55, 60, 65, 70, 75, 80, 85, 90, 100, 110, 120, 130, 140, 150, 160, 170, and 180 minutes. In various embodiments the retention time can be between any two of the above specified retention times.

In various embodiments the MSW entering the rotating cylinder can be saturated. In various embodiment the amount of saturation of the MSW entering the rotating cylinder can be about 10, 15, 20, 25, 30, 35, 40, 45, 50, 55, 60, 65, 70, 75, 80, 85, 90, and 95 percent by weight. In various embodiments the amount of saturation can be between any two of the above specified percentages.

In various embodiments within traversing a predefined longitudinal distance after entering the rotating cylinder, the MSW can be saturated to any of the immediately prior paragraph's percent by weight saturation (and/or ranges of saturation). In various embodiments the predefined distance can be 1, 2, 3, 4, 5, 6, 7, 8, 9, 10, 15, 20, 25, 30, 35, 40, 45 and 50 feet. In various embodiments the amount of saturation can be between any two of the above specified predefined distances. In various embodiment the amount of saturation of the MSW can be about 10, 15, 20, 25, 30, 35, 40, 45, 50, 55, 60, 65, 70, 75, 80, 85, 90, and 95 percent. In various embodiments the amount of saturation can be between any two of the above specified percentages.

In various embodiments, within traversing a predefined percentage of the overall longitudinal length of the rotating cylinder, the MSW can be saturated to any of the second most immediate paragraph's percent by weight saturation (and/or ranges of saturation). In various embodiments the predefined longitudinal percentage can be 1, 2, 3, 4, 5, 6, 7, 8, 9, 10, 15, 20, 25, 30, 35, 40, 45, and 50 percent. In various embodiments the amount of saturation can be between any two of the above specified predefined longitudinal percentages. In various embodiment the amount of saturation of the MSW can be about 15, 20, 25, 30, 35, 40, 45, 50, 55, 60, 65, 70, 75, 80, 85, 90, and 95 percent. In various embodiments the amount of saturation can be between any two of the above specified saturation percentages.

In various embodiments the method and apparatus can agitate continuous MSW by rotation lifting and dropping the MSW (which can be water saturated) at about less than or equal to 2, 4, 6, 8, 10, 12, 14, 16, 18, and/or 20 revolutions per minute. In various embodiments the rotation can be between any about any two of the above specified amounts.

In various embodiments the rotating cylinder's or drum's longitudinal length "L" can be about 25, 30, 35, 40, 45, 50, 55, 60, 65, 70, 75, 80, 85, 90, 95, 100, 105, 110, 115, 120, 125, 130, 135, 140, 145, and 150 feet. In various embodiments the length can be between any about any two of the above specified amounts.

In various embodiments the vessel diameter can be about 4, 6, 8, 10, 12, 16, 18, and 20 feet. In various embodiments the diameter can be between any about any two of the above specified amounts.

In various embodiments the rotating vessel can be pitched or sloped downward at about 1, 2, 3, 4, 5, 6, 7, 8, 9, 10, 11, 12, 13, 14, and/or 15 degrees. In various embodiments the pitch or slope can be between any about any two of the above specified amounts. The pitching and/or sloping of the rotating vessel can create a controlled and manageable substantially continuous lateral (e.g., generally in a longitudinal direction) flow through the interior of the rotating vessel.

In various embodiments the rotating vessel can be pitched or sloped in an uphill configuration at about 1, 2, 3, 4, 5, 6, 7, 8, 9, 10, 11, 12, 13, 14, or 15 degrees. A helix would be used in this configuration to facilitate uphill flow and to facilitate desired retention time while lift plates or buckets may still be utilized for increased agitation.

In various downward sloped rotating vessel applications, baffle plates, mounted perpendicular to process flow may be installed to increase retention time.

In various embodiments the rotating vessel can be horizontal, with a helix utilized to facilitate desired flow rate and related retention time while lift plates or buckets may still be used to increase agitation.

Many U.S. markets are unable to support MSW processing systems requiring significant water addition during treatment. For example, prior art MSW processing systems in a 1,400 ton per day configuration can require over 200,000 gallons of water per day, or about 150 gallons per minute, 24 hours per day.

In one embodiment one or more screw presses can be used to recover water from the screen separated MSW derived biomass in order to substantially reduce overall water consumption in the MSW treatment process. Using recycled water recovered from the pulped MSW derived biomass, as pulping water addition to the rotating cylinder greatly reduces or eliminates the amount of outside water required for pulping treatment and recyclables recovery.

In one embodiment the method and apparatus substantially prevents drying of the pulped MSW (while being pulped and sanitized in the rotating cylinder) to facilitate necessary pulping of paper and paperboard and subsequently recovers water from the pulped MSW for re-use in the rotating cylinder.

In various embodiments the method and apparatus can recover water from pulped MSW. In various embodiments the average percent of water moisture of the largely organic pulp MSW exiting the rotating cylinder is about 50, 55, 60, 65, 70, 75, 80, and 85 percent. In various embodiments the average exiting moisture content can be between any two of the above specified percentages.

In one embodiment about one half of the moisture in now pulped MSW exiting the rotating cylinder can be recovered and processed for re-use in the rotating cylinder as make-up pulping water. In various embodiment the amount of recovered moisture from the pulped MSW exiting the rotating cylinder can be about 10, 15, 20, 25, 30, 35, 40, 45, 50, 55, 60, 65, 70, 75, 80, 85, 90, 95, 100, 105, 110, 115, and 120 percent. In various embodiments the amount of recovery of moisture can be between any two of the above specified percentages. In various embodiments the amount of recovery of water can be greater than 100 percent of necessary pulping water because the input MSW has a high water content and a relatively small amount of feed saturation steam/water need be used.

In one embodiment moisture recovery can be by mechanical dewatering methods acting on the exiting pulped MSW. In one embodiment a screw press and/or centrifuge can be used. In other embodiments micronizer drying systems can be used for breaking apart and drying pulped MSW (such as by use of the "Device For Comminution" disclosed in U.S. Pat. No. 6,024,307 which patent is incorporated herein by reference). In various embodiments water recovery can be used in connection with the water removed by the micronizing drying systems and such recovered water can be recycled in the process of pulping MSW. In other embodiments recovery of condensate, dissolved air flotation, membrane filters, and/or anaerobic digestion technology can be used.

In one embodiment, upon exiting from the cylinder, the now pulped MSW can be screen separated (in one embodiment immediately).

In various embodiments a portion of the original process heat is retained in the recycled water. In various embodiments the amount of retained process heat can be about 10, 15, 20, 25, 30, 35, 40, 45, 50, 55, 60, 65, 70, 75, 80, 85, 90, and 95 percent. In various embodiments the amount of retained process heat can be between any two of the above specified percentages.

In various embodiments heat can be captured from recycled pulping process water passing through an anaerobic digester which digester can remove organics from the process water. In one embodiment a moderate temperature (about 100 degrees Fahrenheit) of the anaerobic digestion discharge water can substantially reduce the amount of pre-heat required for the process makeup water used by the rotating cylinder during pulping—which process makeup water can be heated to approximately 205 degrees Fahrenheit prior to entering the rotating cylinder for pulping. In other anaerobic processing causes the recycled pulping water to be at about 80, 85, 90, 95, 100, 105, 110, 115, 120, 125, 130, 135, 140, 145, 150, 155, 160, 165, 170, and 175 degrees Fahrenheit. In various embodiments the recycled pulping water can be between any two of the above specified temperatures.

In one embodiment organics removal from recovered water via anaerobic digestion produces methane gas which can be used to partially fuel a boiler used to generate steam and cleans the recycled water for continued use in pulping the MSW.

Another advantage of controlled, low temperature treatment is the ability to avoid crystallization of cell structure of the cellulose and hemicellulose component of the organic pulp. As a potential feedstock for cellulosic hydrolysis processes (to produce ethanol, butanol, methanol or synthetic gasoline), such crystallization is in some cases, undesirable. Process yields for cellulosic ethanol and other cellulosic specialty chemicals can be significantly reduced by high temperature crystallization, as sugars become more difficult to separate and extract. Many vendors seeking cellulosic feedstocks for hydrolysis based processes may be less interested in organic feeds which have been exposed to higher temperatures such as organic pulp derived from higher temperature batch autoclave processing.

In various embodiments the amount of crystallization of cell structures of cellulose and hemicellulose in the pulped MSW is less than 2, 5, 10 15, 20, 25, 30, 35, 40, 45, and 50 percent. In various embodiments the amount of crystallization can be between any two of the above specified percentages.

Low temperature processing of MSW also avoids volatilization of organics which have relatively low flash points. High temperature systems volatilize organics within the waste stream which may expose recycle facility workers to inhalation dangers or potential explosion hazards. Processing at high temperature also results in significant additional odor issues and associated higher odor mitigation costs for the processing facility, or resulting vapors and/or odors may result in facility closure due to aforementioned unsafe working conditions or complaints by neighbors. Such unnecessary volatilization further results in undesirable organics contamination of recovered condensate, resulting in high wastewater treatment costs.

In various embodiments the method and apparatus provides low temperature MSW pulping and separation avoids shrinkage of plastics, and although touted by existing high temperature MSW sterilization and recycling technologies as beneficial relative to sterilization, such deformation is highly detrimental to plastics recycling efforts. In high temperature applications, plastics discolor, and will shrink and wrap around un-desirable organic and inorganic contamination, reducing value and in some cases eliminating potential for recycling altogether. Rotating cylinder treatment systems can be good candidates for emerging depolymerization technologies which facilitate recovery of all mixed plastics from MSW, including film plastics and unwanted chlorinated plastics, in addition to more frequently recovered and valuable plastics such as PET. With these newly developing technology applications, plastics may be recovered for reuse and not for combustion, gasification or pyrolysis. Consequently the method and apparatus has the ability to better separate high value plastics and should lead to higher levels of plastics re-use and increased carbon emissions avoidance compared to prior art systems.

BRIEF DESCRIPTION OF DRAWINGS

FIG. 4 is a wire frame side view of one embodiment of a rotating cylinder that can be used in the method and apparatus.

FIG. 5 is a flight pattern of one embodiment of lifting flutes or upsets.

FIG. 6 is an enlarged wire frame side view of the first end of the rotating cylinder shown in FIG. 4.

DETAILED DESCRIPTION

Figure 1:
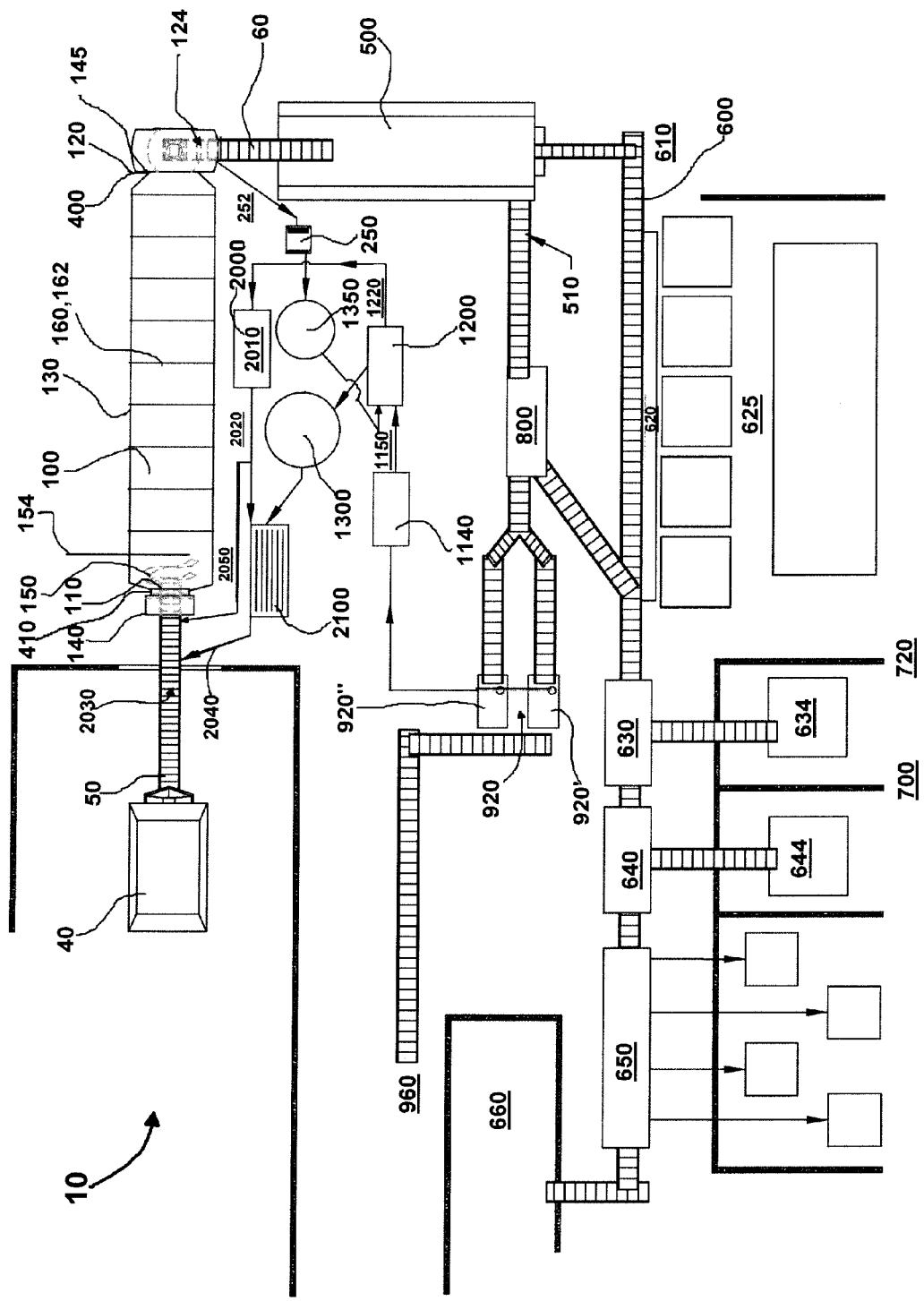
FIG. 1 is an overall schematic view of one embodiment of the method and apparatus showing operation without a screw press.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate system, structure or manner.

In one embodiment, MSW can be removed from garbage bags in a de-bagging device 20 in order to separate in a wire/textile sorter 30 relatively dry textiles prior to potential additional shredding and hot pulping water addition. Textiles removal prior to shredding and water addition is advantageous to the overall process due to one or more of the following factors:

(1) Hot Water addition rates and associated costs may be lowered due to removal of highly absorbent textiles;

(2) Screen separations will be more efficient without bulky textiles which block screen surfaces;

(3) Plastics, ferrous metals, aluminum sorting systems will be much more efficient without wet textile interference;

(4) Conveyance systems will be more efficient without bulky textiles which attached to shredded metals and other textiles to form difficult to separate recyclable masses;

(5) Recycle textile values are increased due to lower drying cost and/or dryness of recycle textile product;

(6) Labor cost for textile sort is decreased due to larger, dryer and less dense textile physical characteristics prior to shredding and water addition.

In one embodiment MSW can be shredded to under 12 inches with a commercially available reducer (shredder) 40 commonly utilized in the municipal waste processing markets. A single shredder processing approximately 30 tons per hour will adequately feed a standard 700 ton per day with the method and apparatus.

Shredded MSW is introduced into a sloped conveyor which feeds an insulated, slightly downsloped feed conveyor 50, which is fitted with steam injection and hot water addition nozzles. This conveyor 50 will feed the rotating cylinder 100 with a constant flow of pre-shredded, saturated, pre-heated MSW. Water addition can be at approximately 205 degrees Fahrenheit and is added at a ratio of approximately 50% by weight.

Conveyor 50 can be a sloped belt conveyer which can be shrouded.

In one embodiment a rotating cylinder 100 can be used with a base system size to process approximately 700 tons of shredded, mixed household MSW and some or all of approximately 350 tons of hot water addition in a 24 hour period. In one embodiment cylinder 100 can be approximately 70 feet long and 11 feet 9 inches in diameter with a main body of stainless steel construction. It can be horizontally mounted at a down slope pitch of approximately two (2) to six (6) degrees on roller bearings and gear driven by a 150-200 horsepower hydraulic motor or standard electric motor.

In one embodiment the rotating cylinder 100 can be inclined at a slight angle to the horizontal. In various embodiments the angle of inclination 105 can be about 1, 2, 3, 4, 5, 6, 7, 8, 9, 10, 12, 14, 16, 18, and 20 degrees. In various embodiments the angle of inclination can be between any two of the above specified angles. In various embodiments the angle of inclination can be varied between any two of the above specified angles.

In another embodiment a rotating cylinder consisting of 6 to 12 flat, welded stainless steel panels can be used in a base system to process approximately 700 tons of shredded, mixed household MSW in a 24 hour period. This cylinder can be 8, 10, 12, 14, or 16 feet in diameter or in between, based upon the individual width of each like welded panel. This system can be horizontally mounted on a downslope pitch of approximately two (2) to six (6) degrees on roller bearings and gear driven by a standard electric or hydraulic motor or alternatively by a series of urethane tires and with up to four separate drive motors of 25 to 75 horsepower each. This particular system offers drive system redundancy which is beneficial to continued operations during temporary outage of one such drive motor.

The sloped conveyor and insulated, feed conveyor 50 can transfer MSW from the shredder 40 to the rotating cylinder 100 via a mechanical seal 200, which is sealed around the feed end 110 of the rotating vessel 100, dis-allowing unwanted air from entering the cylinder 100 or loss of heat from the well insulated and sealed cylinder 100.

In one embodiment rotating cylinder 100 can be insulated along its longitudinal length to reduce and/or minimize heat loss of MSW from the interior of cylinder 100 while MSW is traveling along the longitudinal length "L" of cylinder 100. Insulation is conventionally available such as calcium silicate insulation.

In one embodiment a helix 150 will move the shredded MSW away from the inlet area 110 of the cylinder for the initial 3-5 feet (for depth "D") entering the cylinder 100 and toward lifting flutes 160 inside the main barrel 130 of the rotating cylinder 100. These flutes 160 or lift plates will lift the now saturated MSW, and drop the material from high in the 11 foot 9 inch diameter barrel in order to maximize agitation and facilitate re-pulping (breaking apart) of all paper and paperboard in the MSW. These stainless steel flutes 160 are also designed with a specific angle of bend 163, in conjunction with the degree of pitch of the overall rotating cylinder 100, to facilitate and regulate slow, gradual flow through the stainless steel rotating cylinder 100, and ensure a minimum 30 minute retention time. A series of baffles may also be added to increase MSW retention time in the vessel if necessary to prevent short circuiting or retention time of less than 30 minutes. The drive system 300 also employs a variable speed drive in order to further control degree of agitation and maintenance of minimum retention time.

In one embodiment rotating cylinder 100 can have a parallel flow steam addition 410 at the inlet end 110 of the cylinder 100, which is drawn though, toward the MSW outlet end 120 via addition of a negative pressure drawn from above the rotating cylinder 100 by blower 250. Discharge end 120 can include a drum discharge 124.

Figure 2:
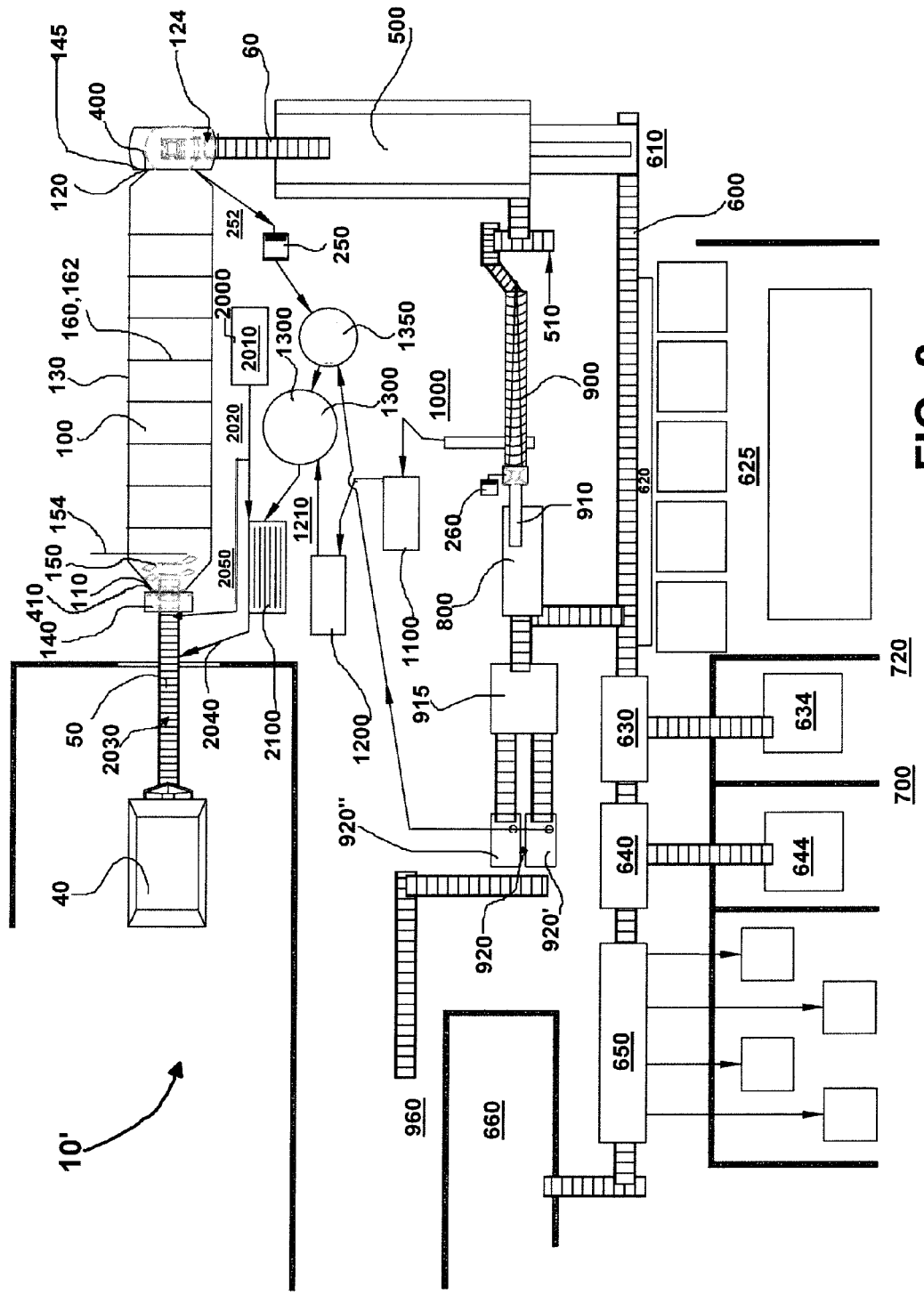
FIG. 2 is an overall schematic view of a second embodiment of the method and apparatus shown operation with a screw press.
Figure 3:
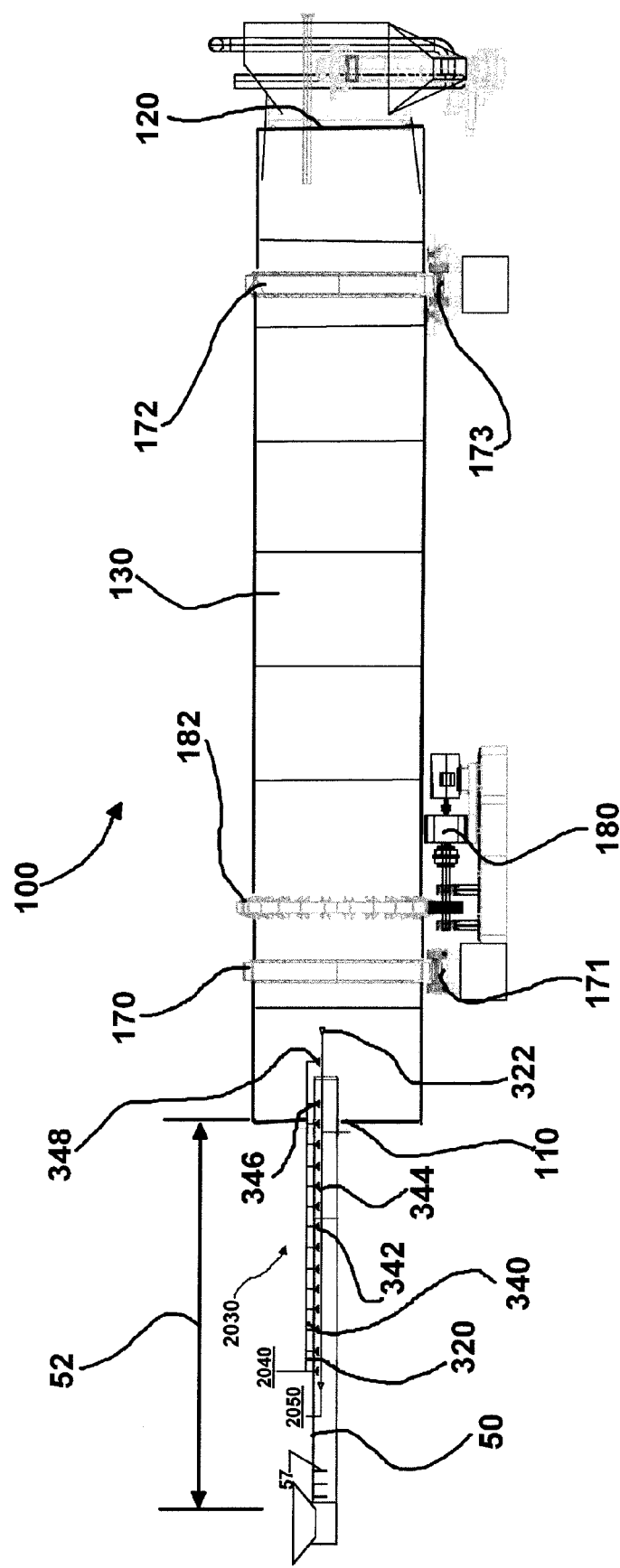
FIG. 3 is a side view of another embodiment of a rotating cylinder with inlet conveyor attached.
Figure 7:
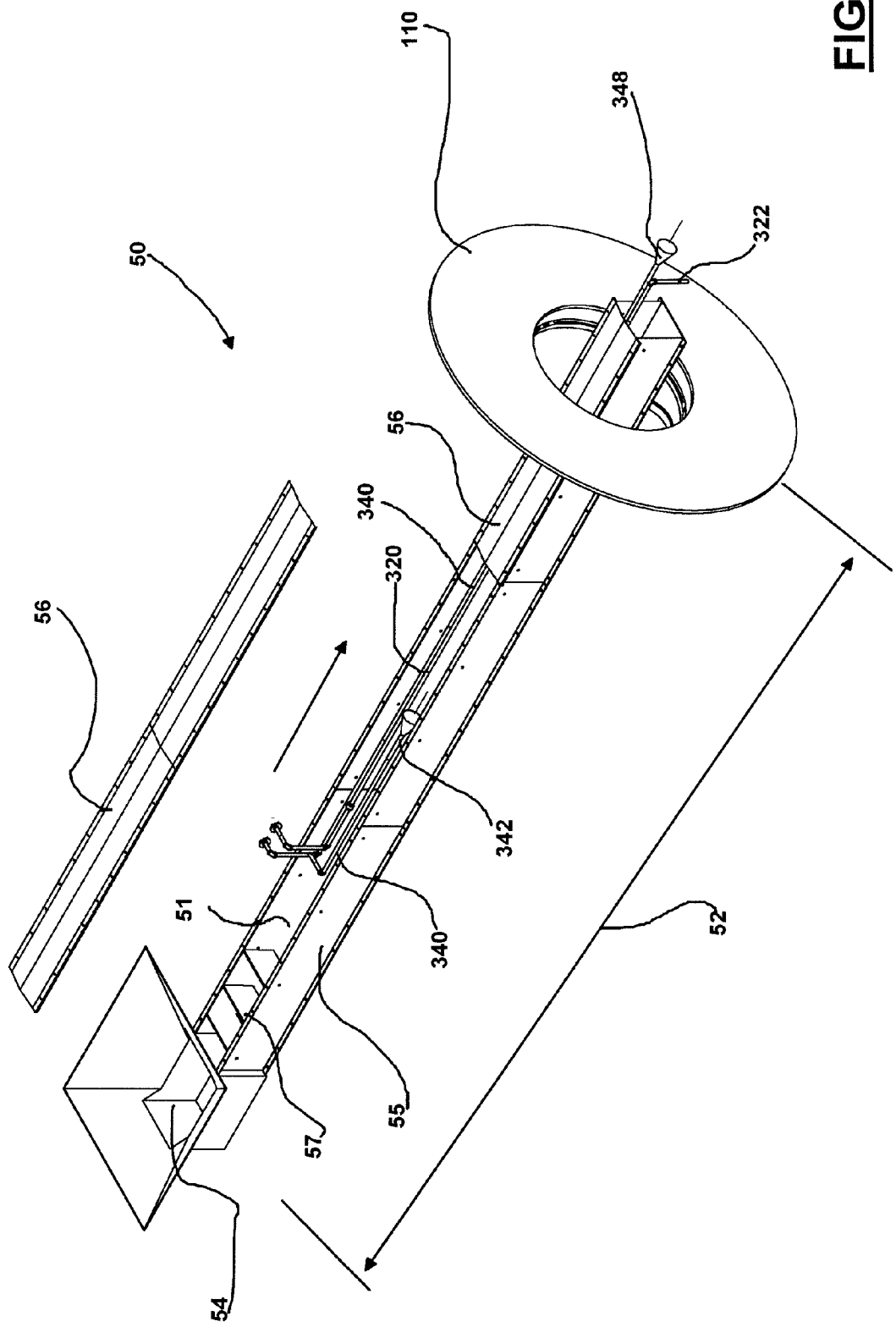
FIG. 7 is a perspective view of one embodiment of a shrouded inlet conveyor.
Figure 8:
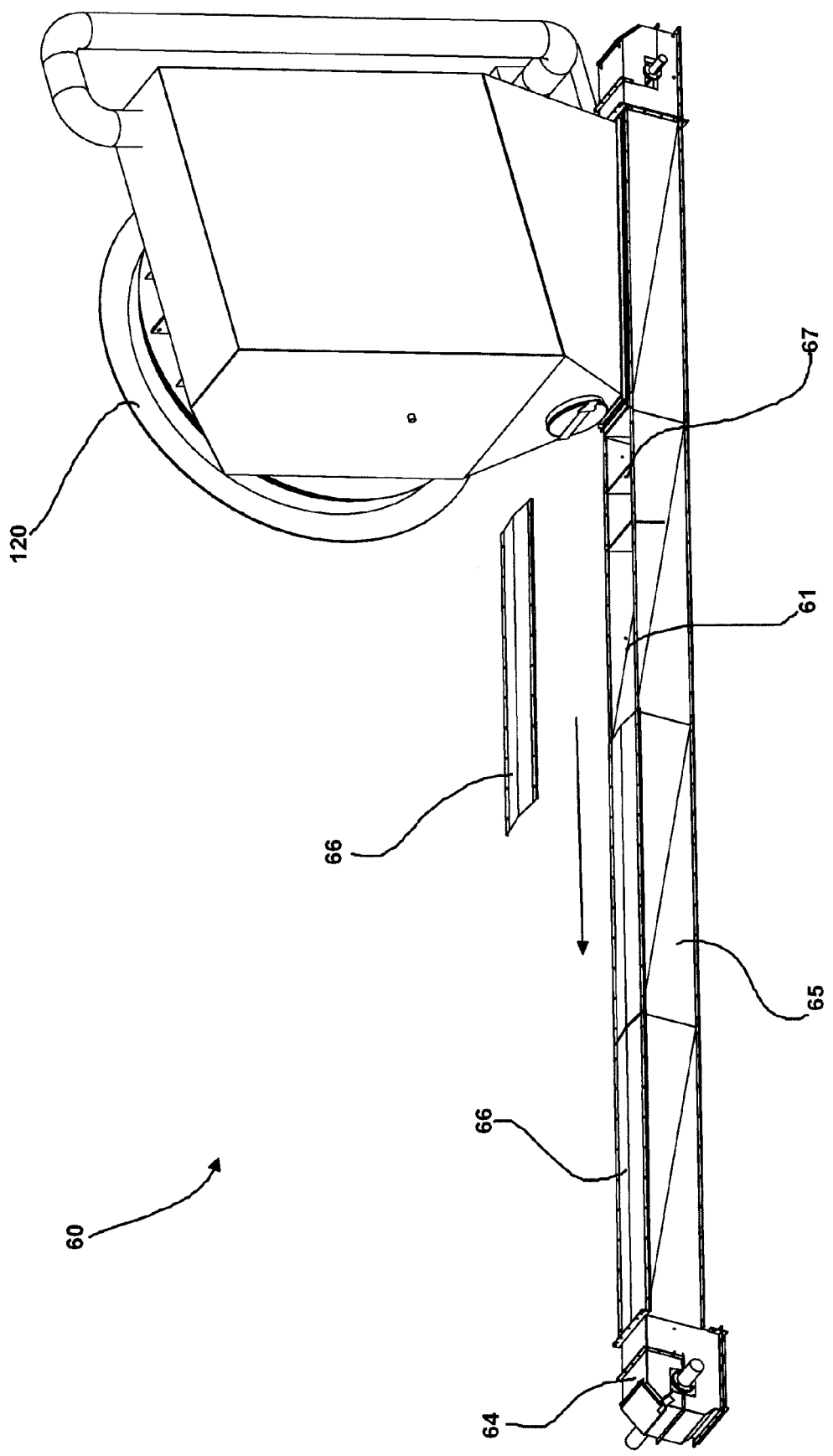
FIG. 8 is a perspective view of one embodiment of a shrouded outlet conveyor.

In one embodiment rotating cylinder 100 can have a counter flow steam addition 400 at the discharge end 120 of the cylinder 100, which is drawn though, toward the MSW inlet end 110 via addition of a slight negative pressure drawn from above the rotating cylinder 100 inlet 110 by a small externally mounted blower 250' which is mounted close to the inlet 110 of cylinder 100 (such mounting configuration is not shown in FIG. 1 or 2, but can be obtained by blower 250 being moved to inlet 110 side of cylinder 100).

In one embodiment steam addition and negative pressure draw may be reversed in order to minimize potential steam and heat loss from the inlet end of the vessel where some steam and hot water are added via the feed conveyor.

A small volume of steam may be recovered which will condense and be recovered within the recycle water processing systems. Saturated steam addition will be provided by either existing steam systems 500 or a provided package boiler to maintain a minimum temperature of 180 degrees Fahrenheit and maximum temperature of 210 degrees Fahrenheit in the MSW being processed within the rotating cylinder 100, resisting exposing the treated MSW to higher or lower temperatures. The early upstream introduction of hot water and steam blanket to the pre-shredded MSW in the insulated sloped conveyor 50 and counter flow steam 400 through the rotating cylinder 100 are design components which maintain the relatively low, aforementioned range of temperature throughout the prescribed minimum 30 minute MSW pulping process in order to maximize sanitation of the waste prior to separations and packaging of numerous recycle commodities.

In one embodiment, a mechanical seal such as a rotating vane sealing device 145 may be added to the upstream end of the saturation/feed conveyor to better seal the system against heat loss. A second mechanical seal such as a rotating vane seal 140 may be added to the bottom of the drop box for the purpose of heat loss reduction. The type of gasketed rotating vane seal proposed does not allow buildup of pressure within the vessel, in addition to the constant vacuum pulled on the vessel to facilitate steam flow through the vessel.

After minimum 30 minutes retention time in the constant flow rotating cylinder 100, the sanitized, pulped MSW will be discharged at end 120 via another mechanical seal 145 downward and into a drop box and fully contained insulated sloped conveyor 60, to further maintain minimum temperature and minimize intrusion of unwanted air to the saturated steam environment of the rotating cylinder 100, feed 50 and discharge 60 conveyors. Conveyer 60 can be an sloped belt conveyer which can be shrouded.

This insulated sloped conveyor 60 will discharge directly into a large trommel screen 500 capable of the entire capacity of the upstream shredding 40 and rotating can cylinder 100 after necessary water addition. In one embodiment trommel 500 can include a 40 foot by 10 foot barrel.

In one embodiment a primary trommel screen equipment 500 can include an approximately 10 feet diameter barrel with 40 linear feet of screen surface. This existing screen separation technology will be used to separate re-pulped paper and paperboard, and other miscellaneous small diameter (less than approximately 1.5 inches) organic and inorganic materials from larger recyclables and textiles which do not size reduce during method and apparatus 10 operations.

The larger materials can be conveyed 600 from the primary trommel screen 500 to secondary screen separations and magnetic 630 and eddy 640 current systems for ferrous 634 and aluminum 644 separations respectively, and for final automated optical and density separation of plastics 650. The plastics are conveyed to the rejects 660. All oversized recycling operations utilize existing municipal solid waste recycling equipment commonly found in "single stream" or "source separated" materials recovery facilities or MRFs. However, in this unique new configuration, a much higher overall recovery of recyclables is achieved as the complete MSW stream is processed for recycling and not just the materials which are currently source separated for costly curbside collection, by a fraction of the general public. This easy and low cost recovery of recyclables from all mixed waste is largely due to the screen removal of food waste, yard waste and re-pulped paper and paperboard, which is facilitated by the pre-removal of dry textiles and the complete pulping action within the continuous flow rotating treatment cylinder.

In one embodiment, shown in FIG. 2, once screened to under ½ inch, a conventionally available screw press 900 (or presses) can be employed to dewater the well screened, MSW derived biomass. Screw press 900 can be used to reduce moisture content in the largely fibrous organic pulp from approximately 75% water to around 45% water and to recover filtrate for treatment and re-use in the rotating cylinder 100.

High water content exiting pulped MSW from rotating cylinder 100, and the immediate processing and reuse of large quantities of screw press filtrate 1000 is important to the method and apparatus. Another identified benefit of the heated water addition to the raw MSW rotating cylinder 100 feed is that the processed recycle filtrate actually acts as a clean water wash for the organic, largely cellulosic pulp recovered from mixed household and commercial MSW.

In one embodiment method and apparatus 10', recovered screw press filtrate 1000 initially contains approximately 1% to 5% suspended solids. Screw press filtrate 1000 will be pumped into a dissolved air floatation system 1050. In system 1050, suspended solids and oil are floated in a water tank/weir effectively separating water (80%-90%) from undesirable oil and solids by introduction of tiny air bubbles to the water tank. Oil and suspended solids attach to the air bubbles and overflow a weir structure along with about 10%-20% of the water flow and are further processed by a centrifuge 1100, where suspended solids and oil will be further concentrated and recovered. These solids are typically clay, sand and glass fines and small paper fibers which are combined with cooking oils and other organic oils which may be delivered to a bio-diesel refining facility, gasification or pyrolysis unit, or other environmentally responsible reuse.

In one embodiment the undersized screenings 510 from trommel 500 operations can be screened in a second stage such as by a vibratory and/or multi phase screening system 800, which finish screen can be a conventionally available screening such as that sold by IFE (Innovationen Fur Eistigs-system out of Austria) under the name TRISOMAT SCREEN.

In one embodiment, the underflow water in dissolved air flotation system 1050, combined with centrate water from centrifuge 1100 operations will be delivered to an aerobic or anaerobic digestion system 1200, for treatment of high Biological Oxygen Demand (BOD) and high Chemical Oxygen Demand (COD). This system's 1200 cost will be significantly reduced by the previous use of the dissolved air floatation system 1050 which system 1050 will begin the process of BOD and COD reduction by recovery of suspended organic solids and in particular, oils from the screw press filtrate. The presence of oils in some anaerobic digestion system is detrimental to the health of the microorganisms which clean up the water in their production of methane. The anaerobic digestion system 1200 cost is further mitigated by the production of this methane gas where the produced methane gas 1220 can be used as a boiler fuel for method and apparatus 10. Upon exiting digester 1200 at elevated temperature of approximately 100 degrees Fahrenheit, the processed filtrate can be tanked 1300, with potential addition of waste heat from renewable power generation, steam production or pulp drying operations. This in order to minimize or eliminate virgin steam use in recycle water heating in a pulping water heat exchanger 2100.

In one embodiment a reverse osmosis or alternative digestion system may be employed which is not inhibited by suspended organic solids or oils and grease and which may eliminate the potential use of dissolved air floatation or centrifuge systems.

In one embodiment a closed loop steam heating system 2100 can be used to minimize boiler feed water makeup water consumption by returning "clean side" or "steam side" fluid (e.g., condensate) from heat exchanger 2100 to boiler feed water tank 2010 in a closed loop. This heating through heat recovered of treated and recycled screw press filtrate facilitates a closed loop on the "dirty side" of the heat exchanger for hot water assisted pulping of the paper and paperboard components of the MSW, once again, with the recovered screw press filtrate. Once heated to above 205 degrees F. by the heat exchanger, the recycled pulping water is added 2020 to the pre-saturating, pre-heated feed conveyor and additionally 2030 to the initial MSW entry point into the CRTC.

In one embodiment the hot water can be is added 2030 to the feed conveyor and/or feed end 110 of rotating cylinder 100 at about 205 degrees Fahrenheit to begin the sanitation process and to saturate the paper and paperboard component of the shredded waste to facilitate pulping of paper and paperboard fractions of mixed municipal solid waste.

Compressed screw press 900 filtercake 3010 discharge, with a solids content of about 55% is broken apart by a simple lump breaker 910 (one per each screw press), in order to break apart screw press filtercake 3010 and in order to feed loose and separated organic fibers and remaining small diameter inorganic waste into density separation equipment.

In another embodiment an air educator may be used to break apart the screw press filtercake with the excess air from this system ducted to a high volume dust collection system already utilized for the adjacent density separation equipment (destoner) 915.

A flailing devise, similar in nature to a flail mower, commonly used for grass cutting, may be designed and manufactured in order to break apart screw press filtercake and to facilitate separation of entrained dense inorganics by destoner density separation.

In one embodiment, after lump breaking technology has been employed, the loose fiber with inorganic contamination can be fed to a vibrating screen conveyor 1450. This conveyor 1450 employs a fine mesh screen to remove sand, other silicates and fine grained inorganics which would not be removed by subsequent density separation equipment which effectively removes larger pieces of glass, batteries, gravel and other inorganic contamination. Such fine grained material is problematic to the selected density separation equipment as it passes through the screen surface which is designed to convey dense inorganics on its surface and not have inorganics pass through it. Heating value will be increased and residual ash content will decrease in thermal processes such as gasification and pyrolysis. This vibratory screening process ultimately results in significant reduction of inorganic content of processed biomass, beyond previous achievable levels achieved by dry inorganics removal systems, and creating a highly desirable inorganics free biomass feed stock for numerous emerging biomass "conversion technologies".

In yet another novel embodiment of method and apparatus 10, an air destoner 915, commonly used for density separation of rocks and sand from seed or grain is used to separate mechanically dewatered and now light organic biomass pulp from denser, inorganic fractions of the undersized screenings.

The mechanical dewatering of MSW derived biomass to less than 50% moisture is necessary for this specific density separation equipment selection and in selected air destoner in order to produce sufficient density differential for efficient separation of damp organic pulp from dense inorganic waste. Such inorganics for separation include broken glass, nuts and bolts, sand, gravel, tiny batteries or other unwanted inorganic contamination. Sanitized, inorganics free pulp is now available for further processing or direct use in the production of renewable power, cellulosic ethanol, or other cellulosic specialty chemicals such as butanol, leveulinic acid, furfural, methanol, diesel or formic acid, based on specific conversion technology application.

In one embodiment a specific air drying and biomass deformation/size reduction technology, micronizer 920 (or 920' and/or 920") can be used for additional size reduction and biomass deformation for selected cellulosic chemicals production. The selected size reduction and biomass deformation technology improves surface to pore area and reduces chrystallinity, which reduces or eliminates more costly feedstock pre-processing procedures commonly used in biological conversion technologies. Cellulosic ethanol clientele have also indicated that biomass deformation will potentially lead to significantly lower chemical pre-treatment and specialty enzyme costs. Sugars are more easily accessed and separated from the cellulose and hemi-cellulose structures and associated lignin bonds due to the micronizer 920 (920' and/or 920") equipment's capability to vastly increase surface area through aggressive mechanical size reduction and actual rupture of cellulose structures.

The method and apparatus 10 sanitation, both initially in the rotating cylinder 100 and again in the micronizer 920 is also a major value adder for vendors who introduce specialty strains of yeast or enzymes to their cellulosic feed stocks, as they desire all biological activity within the feed stock to be eliminated prior to their own conversion of the cellulosic materials. All of the aforementioned costs saving advantages are further supplemented by associated increased product yields per given unit of cellulosic feedstock.

The micronizer 920 (920' and/or 920") is an air/mechanical equipment process which reduces particulate sizing in biomass feed stocks and which also performs biomass deformation on a cellular level. This system may be utilized for specific conversion technology vendors for biomass deformation as mentioned above, or due to desired emphasis on obtaining higher dry solids content. The micronizer 920 (920' and/or 920") may facilitate low drying costs for a number of thermal conversion technologies such as gasification or pyrolysis. These biomass conversion technologies may be used for production of renewable heat and power, or for the production of renewable liquid biofuels or specialty chemicals via gas to liquids technologies.

Should landfill methane be available at no or very low cost, a gas based drying system may offer savings over an electricity consuming air drying system such as micronizer 920 (920' and/or 920"). Availability of waste heat may also result in scoping of a waste heat dryer rather than the micronizers in certain applications. Additional drying or biomass densification systems in the final stages of the method and apparatus 10 can be used based on desired particulate sizing and desired moisture content relative to transportation logistics, storage considerations, pneumatic conveyance, feed stock mixing, or biomass deformation preference. All potential technology applications will be considered taking into consideration potential availability of waste heat, landfill gas or digestor methane.

In another embodiment, micronizer 920 (920' and/or 920") may be used immediately after secondary screening system 800, in conjunction with waste heat addition to makeup air to the micronizer 920 (920' and/or 920"), along with the addition of a discharge air condenser 930 for micronizer 920 system air discharge, in order to utilize the micronizer's 920 drying capabilities, and micronizer's 920 capability to separate recoverable moisture from the MSW derived biomass with less suspended solids and oil contamination. This approach would be used as a means of eliminating screw press 900, delumping equipment (910), density separator/destoner (915) and significantly reducing water treatment cost associated with dissolved air floatation equipment 1050, centrifuge 1100, and anaerobic digestion systems 1200.

In one embodiment, low temperature rotating cylinder 100 implementation allows for screen separation of rigid and film plastics from organic pulp in processed MSW with the pulp to be used in numerous emerging thermal conversion technologies. Due to the method and apparatus 10 design efficient separation of inorganics and plastics and the overall pulp washing process, thermal technologies should enjoy lower chlorides and sulfur compound emissions, and produced power or biofuels should qualify as 100% renewable under recently promulgated RFS2 Federal Legislation. The vast majority of current MSW derived feed stocks for power production include plastics with the paper and other organic fractions of MSW in order to boost heating value. The method and apparatus 10 employs separation of plastics for recycling to displace crude oil or for production of recycle plastic products (which in some cases additionally replace wood products).

In one embodiment landfill diversion associated with low cost method and apparatus 10 implementation will result in immediate and significant reduction in landfill fugitive methane emissions, production of hazardous landfill leachate and attraction of vermin and birds to organic waste landfills. Wind blown litter and odors associated with the daily landfill of raw garbage are also eliminated. Recovery and recycling of metals, glass, plastics and textiles will each, in varying degrees, contribute to reductions in greenhouse gas emissions. Possibly the largest reduction in greenhouse gas emissions resulting from implementation of method and apparatus technology application will be the use of the recovered organic biomass fraction of MSW for the production of renewable power or biofuels to displace non-renewable electricity or liquid transportation fuels.

In one embodiment the ambient pressure, constant flow method and apparatus 10 is specifically designed to separate all traditional recyclables for recovery and to produce MSW derived, inorganics free biomass to specification, as feedstock for emerging "MSW conversion technology" applications. Due to economies of scale associated with the constant flow design, value of recyclables, and the diversion of the majority of MSW from costly transportation and landfill, ideal, homogenous feed stocks can be produced at very low or no cost for such emerging biomass conversion technology applications. Due to the values identified above, method and apparatus 10 processed feedstocks may be offered at fixed pricing for long contracting periods of over 10 years which is also due to existing MSW collection logistics, greatly mitigating the financial risk of future feedstock cost and availability for the emerging renewable power and biofuels industry. This synergy of shared value should greatly enhance rapid roll out of this suite of technologies and make a significant and important contribution to carbon emissions avoidance on many levels.

Rotating cylinder 100 can be rotatively mounted on support rollers 171 and 173. Rotating cylinder 100 can be generally cylindrical in shape and mounted so as to be rotatable in either direction on its axis. Rotating cylinder 100 can be provided with contact rings 170 and 172 respectively supported by rollers 171 and 173. Both inlet end 110 and second end 120 of rotating cylinder 100 can be at about ambient pressure.

In one embodiment the typical rate of rotation for rotating cylinder 100 is about 1, 2, 3, 4, 5, 6, 7, 8, 9, 10, 11, 12, 13, 14, and 15 revolutions per minute. In one embodiment a rotational speed can be between any two of the above specified rotational speeds.

In one embodiment the typical rate of rotation for rotating cylinder 100 is between ½ and 30 revolutions per minute; between 2 and 30 revolutions per minute, between 5 and 25 revolutions per minute, between 5 and 15 revolutions per minute, and between 5 and 10 revolutions per minute, and preferably such rotational speed facilitates uniform loading of forces on drive assembly 300 which rotatively drives rotating cylinder 100. In one embodiment variable (such as a high/low) speed control is used for rotating cylinder 100 which can change rotational speed from a low speed, such as ½ to a high speed, such as 10 revolutions per minute. In one embodiment a rotational speed can be infinitely variable.

In various embodiments rotating cylinder 100 can be agitated instead of rotated, where cylinder 100 is partially rotated (i.e., has a span or sweep of agitation) but not completed rotated. In one embodiment the amount of agitation is about 15, 20, 25, 30, 35, 40, 45, 50, 60, 70, 75, 80, 90, 120, 145, 160, 180, 200, 220, 240, and 270 degrees. In one embodiment the sweep of agitation is between any two of the above specified sweeps of agitation.

In one embodiment the rotating cylinder 100 is switched from rotation to agitation, or switched from agitation to rotation.

In one embodiment rotating cylinder 100 is capable of being rotated by means of drive assembly 180 and 182. In one embodiment drive assembly can comprise electric motor 180 and suitable gearing 182 operatively connected to motor 180.

Materials can be loaded through rotating cylinder 100 at first end 110 by shrouded conveyor means 50. Methods of loading materials to be processed include conveyors that extend into the opening, a chute or hopper system utilizing carts, buckets, or tubs that dump materials into the chute/hopper, and/or by hand. Materials need only be dropped in the vicinity of the rotating cylinder inlet 110. Rotation of rotating cylinder 100 will cause the materials to be conveyed towards the second end 120 of rotating cylinder 100.

This embodiment shows a process water control addition system 340 that is supplied with pressurized water used to inject process water into the inlet MSW to be treated. Additionally, steam system 320 can be used to heat the MSW to be treated to a desired process temperature. Heating of the materials to be processed begins as steam is introduced into the insulated feed conveyor and interior of cylinder 100 via steam outlet 322.

In one embodiment the interior of rotating cylinder 100 can be equipped with helical flighting 150 to facilitate agitation and movement of materials as a consequence of rotation of rotating cylinder 100. In one embodiment helical flighting 150 can be offset at an angle from the sidewall of rotating cylinder 100, such that a radial line from the longitudinal center of rotating cylinder and intersecting with a helical flighting would make an angle, such as 14 degrees.

In one embodiment a plurality of upsets or lifting buckets 160 can be attached to the interior of rotating cylinder 100.

Lifting buckets 160 can comprise first section 162 and second section 164. First and second sections 162, 164 can be at angle 165 relative to the wall of rotating cylinder 100 (which can be 90 degrees or other angles). First section 162 can be at angle 163 relative to second section 164 to which it is connected. Such angle 163 can be between about 1 and 89 degrees, between about 15 to 85 degrees, between about 20 to 70 degrees, between about 25 to 65 degrees, between about 30 to 60 degrees, between about 30 to 55 degrees, about 30 degrees, about 45 degrees, or about 60 degrees. Decreasing portion 1750 can be curved or a straight line.

In one embodiment the diameter of rotating cylinder 100 needs to be of a sufficient volumetric capacity to accept a selected quantity of material to be processed, with an additional space of approximately 70% of the volume of the interior diameter of rotating cylinder 100 remaining vacant to allow materials to fall and to mix within rotating cylinder 100 as it rotates. In this embodiment, additional processing capacity can be added to processor 10 by increasing its length "L" or diameter. The ratio of diameter to length is variable and depends upon the amount of material to be processed in a given amount of time in concert with the size and frequency of the agitation mechanisms of the rotating cylinder to insure complete mixing of materials.

In one embodiment the processed materials are then directed to screeners for the separation and recovery of recyclable materials and further potentially to compactors. Other methods and equipment for the separation of component fractions from the processed materials or the further processing of the processed materials as apparent to those skilled in the art and these techniques may also be used for product recovery from the processed materials or for disposal of the residue from the processed materials.

The working fluid in such a vessel does not need to be restricted to just water. Some examples of some fluids used in alternative embodiments include cleaning fluids, reactive gases and liquids, moisture free gases, refrigerated liquids, and solvents.

Such devices can be used for any of a variety of uses including such things as paper pulp, plastic resin drying, coffee bean roasting or treating, food treatment, or rubber processing.

Figure 9:
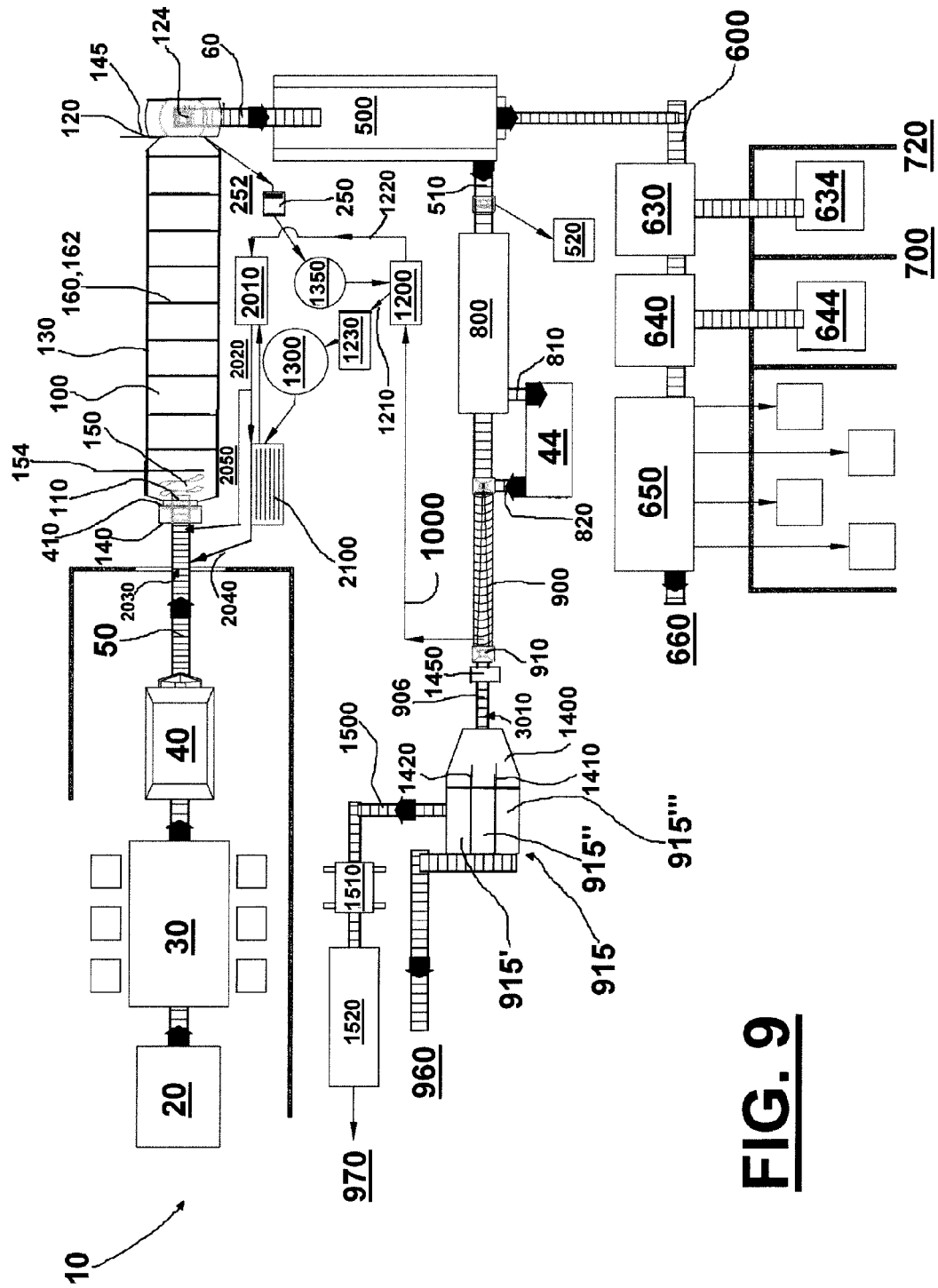
FIG. 9 is an overall schematic view of an alternate embodiment of the method and apparatus.

In one embodiment and as referenced in FIG. 9, screw press filtrate 1000 is pumped to an aqueous digester 1200, to treat this wastewater for re-use in pulping paper and paperboard within the Rotopulper vessel 100, and for production of methane 1220 which reduces steam boiler feed utility costs. Condensate from Rotopulper drum vapor recovery system 252 is also delivered to the digester via a scrubber or knock out tank 1350, to further increase methane production and to eliminate potential steam or odor emissions from Rotopulper vessel operations. Novel use of such a wastewater recovery and treatment process greatly minimizes water use, while minimizing potential use of non-renewable utilities feed to steam boiler, and addressing potential odor concerns.

In one embodiment also referenced in FIG. 9, screw press and Rotopulper condensate wastewater 1210 exiting the aqueous digester is passed through a membrane filter 1230, to treat for potential in-organics contamination. This process disallows buildup of inorganic contamination in wastewater within this digester based wastewater treatment loop, as biological digesters do not remove chlorides or other in-organic contamination.

In an alternate wastewater treatment application, in-organics contamination in screw press filtrate may simply be monitored until levels of contamination approach an unacceptable level of toxicity relative to optimal digester operations, and a batch of wastewater may be diverted to tankage for low flow evaporative treatment to remove in-organics contamination. Upon successful removal of in-organics this water would be returned to the pulping water loop as another batch of in-organics contaminated wastewater is diverted to tankage for low flow evaporative treatment. Such low-flow batch treatment facilitates constant flow operation of pulping systems, dewatering equipment and waste water digester in a low cost, closed loop until by-pass is triggered by high levels of in-organics contamination. This approach greatly reduces sizing of high capital cost evaporative waste water treatment systems effectively lowering overall waste water treatment capital and operating costs.

In one embodiment referenced in FIG. 9, oversized screenings 810, from the Trisomat finish screen 800, are subjected to non-ferrous metals recovery, and then introduced to a shredder 44, for size reduction to less than ½". Shredded, paper and paperboard and small diameter dense in-organics are then re-introduced to screw press feed 820, for dewatering and subsequent density separations. In this manner, little residuals are produced in finish screening, as oversized Trisomat rejects are further processed for re-introduction into feed to ideally suited dewatering and density separations equipment.

From trommel 500 some undersize screenings 510 can be led to metals separation 520. Compressed screw press 900 filtercake 3010 discharge is broken apart by a simple lump breaker 910 in order to break apart screw press filtercake 3010. Filtercake 3010 enters sloped screw conveyor 906 that leads to the vibratory conveyor 1400. The vibratory conveyor homogenizes the material and evenly separates it with separator plates 1410, 1420. These plates evenly divide flow of biomass to three air destoner 915 density separation devices. The heavier separation 1500 from the air destoner is conveyed to a roll crusher 1510 where glass is further crushed and separated from plastics and any remaining organic materials, and conveyed to a glass screening/grading system 1520. The now graded glass aggregate 970 is then stored for transport to recycle glass markets.

Also from the vibratory conveyor, biomass is separated out in the air destoner 915, 915', 915", 915''' and the biomass is lead to recycle 960.

The following is a list of reference numerals:

| Reference Numeral | Description |
| --- | --- |
| 10 | apparatus |
| 20 | bag opener |
| 30 | wire/textile sorter |
| 40 | shredder |
| 44 | shredder |
| 50 | insulated sloped conveyor (e.g., shrouded) |
| 51 | interior |
| 52 | length of conveyor |
| 54 | inlet |
| 55 | walls |
| 56 | shrouded sections |
| 57 | flaps (steam containment flaps) |
| 60 | insulated sloped conveyor (e.g., shrouded) |
| 61 | interior |
| 62 | length of conveyor |
| 64 | outlet |
| 65 | walls |
| 66 | shrouded sections |
| 67 | flaps |
| 100 | rotating cylinder |
| 102 | diameter |
| 105 | angle of inclination |
| 110 | inlet or feed end |
| 120 | exit or discharge end |

| Reference Numeral | Description |
| --- | --- |
| 124 | drum discharge |
| 130 | main barrel |
| 140 | mechanical seal |
| 145 | mechanical seal |
| 150 | helix |
| 154 | end of helix |
| 160 | lifting flutes/buckets |
| 162 | first section |
| 163 | angle |
| 164 | second section |
| 165 | angle |
| 170 | tire/ring |
| 171 | roller |
| 172 | tire/ring |
| 173 | roller |
| 180 | drive motor |
| 182 | drive gear |
| 200 | mechanical seal |
| 250 | blower |
| 252 | drum vapor recovery |
| 260 | blower |
| 300 | drive system |
| 320 | steam system |
| 322 | outlet for steam to rotating cylinder |
| 340 | water addition system |
| 342 | outlet |
| 344 | outlet |
| 346 | outlet |
| 348 | hot water addition to rotating cylinder |
| 400 | counter flow steam addition |
| 410 | parallel or same direction flow steam addition |
| 500 | large trommel screen |
| 510 | undersized screenings |
| 520 | metals separation |
| 600 | conveyor |
| 610 | oversized screenings |
| 620 | hand sort |
| 625 | textiles |
| 630 | magnetic separator |
| 634 | ferrous |
| 640 | EDY separator |
| 644 | aluminum |
| 650 | plastics |
| 660 | rejects |
| 700 | compactors |
| 720 | stock pile |
| 800 | screening separating system (finish screen/TRISOMAT) |
| 810 | oversized items sent to shredder |
| 820 | shredded items now returned to screw press inlet |
| 900 | screw press |
| 902 | press filtrate |
| 906 | conveyor (screw and sloped) |
| 910 | de-lumper/lump breaker |
| 915 | density separate/air destoner |
| 920 | micronizer (e.g., KDS system) |
| 930 | water extraction system/discharge air condenser |
| 960 | recycle biomass |
| 970 | recycle glass aggregate |
| 1000 | screw press filtrate |
| 1050 | dissolved air floatation system |
| 1100 | centrifuge |
| 1140 | kockout tank |
| 1150 | water |
| 1200 | anaerobic digestion system |
| 1210 | water |
| 1220 | methane |
| 1230 | membrane filter |
| 1300 | recycle tank (e.g., recycle water tank) |
| 1350 | scrubber or knockout tank |
| 1400 | vibratory conveyor |
| 1410 | separator plate |
| 1420 | separator plate |
| 1450 | vibratory screen conveyor |
| 1500 | heavies separation |
| 1510 | roll crusher |
| 1520 | glass screening/grading |
| 1750 | decreasing portion |
| 2000 | closed loop heating system (e.g., a package boiler system) |
| 2010 | boiler |
| 2020 | steam |
| 2030 | water add/steam add |
| 2040 | hot water addition |
| 2050 | steam addition |
| 2100 | heat exchanger |
| 3010 | screw press filtercake |

All measurements disclosed herein are at standard temperature and pressure, at sea level on Earth, unless indicated otherwise. All materials used or intended to be used in a human being are biocompatible, unless indicated otherwise.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A method of treating municipal solid waste comprising the steps of:
    (a) providing a rotating cylinder operating at ambient pressure;
    (b) supplying waste to an inlet of the rotating cylinder;
    (c) pulping the waste while inside the cylinder, while live steam is used to maintain a pulping processing temperature between 160 degrees Fahrenheit to 210 degrees Fahrenheit at ambient pressure for a predefined retention time;
    (d) waste exiting from the cylinder and the waste being screened without having been cooked by heating above 210 degrees Fahrenheit; and
    (e) wherein steps "a" through "d" are performed on a continuous basis, wherein in step "b" waste is loaded into the rotating cylinder via a shrouded insulated conveyor and heating of the waste begins as steam is introduced into the insulated conveyor and the interior of the rotating cylinder.

2. The method of claim 1, wherein in steps "c" and "d" the waste includes film plastics, and during steps "c" and "d" shrinkage of these film plastics is avoided, and after step "d" film plastics are separated from the waste.

3. The method of claim 1, wherein the waste after step "d" includes cellulose and hemicellulose and the amount of crystallization of cell structures of the cellulose and hemicellulose is less than 10 percent.

4. The method of claim 1, wherein in step "a" the cylinder has a diameter between about 10 and 16 feet.

5. The method of claim 1, wherein the rotating cylinder has a diameter of between about 12 and 16 feet.

6. The method of claim 1, wherein the rotating cylinder has inlet and outlet ends, and on the inlet end is a helix and from the helix to the outlet end are a series of longitudinally extending lifting plates, the series of lifting plates running continuously in a longitudinal direction from the helix to the outlet end of the rotating cylinder.

7. The method of claim 6, wherein each lifting plate includes first and second planar sections with the first and second planar sections being at an angle relative to each other of between about 15 to 85 degrees.

8. The method of claim 7, wherein the angle relative to each other is between about 30 and 60.

9. The method of claim 1, wherein after step "d" a screw press is used to recover water from the MSW derived, screen separated, pulped biomass waste.

10. The method of claim 9, wherein the recovered water is used in step "b".

11. The method of claim 1, wherein in step "d" the average percent of water moisture of the pulped waste exiting the rotating cylinder is between about 50 and 85 percent.

12. The method of claim 11, wherein about one half of the moisture in the pulped waste exiting the rotating cylinder is recovered and processed for re-use in the rotating cylinder as make-up water.

13. The method of claim 11, wherein the amount of recovered moisture from the pulped waste at the completion of pulping and exiting the rotating cylinder is between about 50 and 95 percent.

14. The method of claim 1, wherein the upper range of the processing temperature is about 188 degrees Fahrenheit.

15. The method of claim 1, wherein the upper range of the processing temperature is about 190 degrees Fahrenheit.

16. The method of claim 1, wherein the upper range of the processing temperature is about 200 degrees Fahrenheit.

17. The method of claim 1, wherein the upper range of the processing temperature is about 205 degrees Fahrenheit.

18. A method of treating municipal solid waste comprising the steps of:
   (a) providing a rotating cylinder operating at ambient pressure;
   (b) supplying waste to an inlet of the rotating cylinder;
   (c) pulping the waste while inside the cylinder, while live steam is used to maintain a pulping processing temperature between 160 degrees Fahrenheit to 210 degrees Fahrenheit at ambient pressure for a predefined retention time;
   (d) waste exiting from the cylinder and the waste being screened without having been cooked by heating above 210 degrees Fahrenheit; and
   (e) wherein steps "a" through "d" are performed on a continuous basis, wherein the amount of crystallization of cell structures of cellulose and hemicellulose in the pulped waste is less than 25 percent.

19. The method of claim 18, wherein in step "c" the retention time of the waste after entering the rotating cylinder is between about 20 and 60 minutes.

20. A method of treating municipal solid waste comprising the steps of:
   (a) providing a rotating cylinder operating at ambient pressure;
   (b) supplying waste to an inlet of the rotating cylinder;
   (c) pulping the waste while inside the cylinder, while live steam is used to maintain a pulping processing temperature between 160 degrees Fahrenheit to 210 degrees Fahrenheit at ambient pressure for a predefined retention time;
   (d) waste exiting from the cylinder and the waste being screened without having been cooked by heating above 210 degrees Fahrenheit; and
   (e) wherein steps "a" through "d" are performed on a continuous basis, wherein in step "d" moisture is recovered from the pulped waste exiting the rotating cylinder for recycling, which is between about 50 and 95 percent, and in step "b" a portion of the original process heat is retained in the recycled water, which portion is between about 50 and 95 percent.

* * * * *